United States Patent [19]
Schreiner et al.

[11] Patent Number: 5,869,537
[45] Date of Patent: Feb. 9, 1999

[54] MACROPHAGE LIPID CHEMOATTRACTANT

[75] Inventors: George F. Schreiner, Los Altos; Louis G. Lange, III, Portola Valley, both of Calif.

[73] Assignee: CV Therapeutics, Palo Alto, Calif.

[21] Appl. No.: 854,145

[22] Filed: May 9, 1997

Related U.S. Application Data

[60] Division of Ser. No. 470,974, Jun. 6, 1995, Pat. No. 5,663,450, and a continuation-in-part of Ser. No. 107,958, Aug. 17, 1993, abandoned.

[51] Int. Cl.[6] .................................................. A61K 31/08
[52] U.S. Cl. ........................... 514/722; 514/826; 436/71; 568/671; 568/687
[58] Field of Search .................................. 514/722, 826; 436/71; 568/671, 687

[56] References Cited

FOREIGN PATENT DOCUMENTS

| WO 90/08777 | 1/1990 | WIPO. |
| WO 93/19807 | 3/1993 | WIPO. |
| WO 94/07542 | 10/1993 | WIPO. |
| WO 95/13295 | 11/1994 | WIPO. |

OTHER PUBLICATIONS

"Secretory Products of Macrophages" by Carl F. Nathan, *J. Clin. Invest.* vol. 79, Feb. 1987, pp. 319–326.

"Adhesion receptors of the Immune System" by Timothy A. Springer, *Nature* vol. 346, Aug. 1990, pp. 425–433.

"Biochemistry of Phagocyte Chemotaxis" by Elliott Schiffmann and John I. Gallin, *Current Topics in Cellular Regulation*, vol. 15, pp. 203–261.

"Platelet–derived Growth Factor and Transforming Growth Factor–B Enhance Tissue Repair Activities by Unique Mechansims" by Glenn F. Pierce, Thomas A. Mustoe, Jane Lingelbach, Victoria R. Masakowski, Gail L. Griffin, Robert M. Senior and Thomas F. Deuel, *The Journal of Cell Biology*, vol. 109, Jul. 1989, pp. 429–440.

"Cloning and Sequencing of the cDNA for Human Monocyte Chemotactic and Activating Factor (MCAF)" by Yasuji Furutani, Hideki Monura, Mitsue Notake, Yoshihiro Oyamada, Toshikazu Fukui, Masaaki Yamada, Christian G. Larsen, Joost J. Oppenheim, and Kouji Matsushima, *Biochemical and Biophysical Research Communications*, vol. 159, No. 1, Feb. 1989, pp. 249–255.

"The Pathogenesis of Atherosclerosis—An Update" by Russell Ross, Ph.D., *The New England Journal of Medicine*, vol. 314, No. 8, Feb. 1986, pp. 488–500.

Editorial Review: "Focal and Segmental Glomerulosclerosis: Analogies to Atherosclerosis", *Kidney International*, vol. 33 (1988) pp. 917–924.

"Studies of Leukotriene $B_4$–Specific Binding and Function in Rat Polymorphonuclear Leukoscytes: Absence of a Chemotactic Response" by Regina A. Kreisle, Charles W. Parker, Gail L. Griffin, Robert M. Senior and William F. Stetson, *The Journal of Immunology*, vol. 134, No. 5, May 1985, pp. 3356–3363.

(List continued on next page.)

*Primary Examiner*—Gary Geist
*Assistant Examiner*—Deborah D Carr
*Attorney, Agent, or Firm*—McDonnell Boehnen Hulbert & Berghoff

[57] ABSTRACT

This invention encompasses a substantially homogeneous lipid chemoattractant released from stressed mammalian tissue which is a neutral lipid which is acid labile and stable to base and is stable in boiling water. This lipid recruits macrophages but not neutrophils to stressed tissue. The invention also encompasses a method for detecting injured tissue by detecting the presence of the above described lipid chemoattractant in body fluids such as urine, serum and saliva. The invention also includes a method for reducing recruitment of macrophages to injured tissue by reducing the amount of the above lipid chemoattractant or by blocking the interaction of this lipid chemoattractant with its macrophage binding site. The addition of this lipid chemoattractant to injured skin tissue promotes healing.

4 Claims, 6 Drawing Sheets

OTHER PUBLICATIONS

Novel effects of 1–0–Hexadecyl–2–Acyl–Sn–Glycero–3–Phosphorylcholine Mediators on Human Leukocyte Function: Delineation of the Specific Roles of the Acyl Substituents by Edward J. Goetzl, Claudia K. Derain, Alfred I. Tauber and Frank H. Valone, *Biochemical and Biophysical Research Communicatons,* vol. 94, No. 3, Jun. 1980, pp. 881–888.

"Mechanisms Underlying the Anti–Inflammatory Effects of Essential Fatty Acid Deficiency in Experimental Glomerulonephritis" by Brad H. Rovin, James B. Lefkowith and George F. Schreiner, *The Journal of Immunology,* vol. 145, No. 4, Aug. 1990, pp. 1238–1245.

"Lysophosphatidylcholine: A Chemotactic Factor for Human Monocytes and its Potential Role in Atherogenesis" by Mark T. Quinn, Sampath Parthasarathy and Daniel Steinberg, *Proc. Nat'l. Acad. Sci. U.S.A.,* vol. 85, Apr. 1988, pp. 2805–2809.

"A Monoculear Cell Component in Experiental Immunological Glomerulonephritis" by George F. Schreiner, Ramzi S. Cotran, Victoriano Pardo and Emil R. Unanue, *The Journal of Experimental Medicine,* vol. 147, (1978) pp. 369–384.

"Modulation of la and Leukocyte Common Antigen Expression of Rat Glomeruli During the Course of Glomerulonephritis and Aminonucleoside Nephrosis" by George F. Schreiner, Ramzi S. Cotran and Emil R. Unanue, *Laboratory Investigation,* vol. 51, No. 5, (1984) pp. 524–533.

"Prevention of Clumerulonephritis and Prolonged Survival in New Zealand Black/New Zealand White $F_1$ Hybrid Mice Fed as Essential Fatty Acid–deficient Diet", by Eric F. Hurd, John M. Johnston, Janice R. Okita, Paul C. MacDonald, Morris Ziff and James N. Gilliam, *J. Clin. Invest.,* vol. 67, Feb. 1981, pp. 476–485.

"Essential Fatty Acids Deficiency Depletes Rat Clomeruli of Resident Macrophages and Inhibits Angiotensin II–Induced Eicosanoid Synthesis", by James B. Lefkowith and George Schreiner, *J. Clin. Invest.,* vol. 80, Oct. 1987, pp. 947–956.

"Essential Fatty Acid Depletion of Renal Allografts and Prevention of Rejection" by George Schreiner, Wayne Flye, Elizabeth Brunt, Ken Korber, and James B. Lefkowith, *Science,* vol. 240, May 1988, pp. 1032–1033.

"The Antiinflammatory Effects of Essential Fatty Acid Deficiency in Experimental Glomerulonephritis" by George F. Schreiner, Brad Rovin and James F. Lefkowith, *The Journal of Immunology,* vol. 143, No. 10, Nov. 1989, pp. 3192–3199.

"Essential Fatty Deficiency During Acute Puromycin Nephrosis Ameliorates Late Renal Injury" by Jonathan R. Diamond, Ivona Pesek, Salvatore Ruggieri and Morris J. Karnovsky, *The American Physiological Society,* pp. F798–F807.

"Essential Fatty Acid Deficiency Ameliorates Acute Renal Dysfuction in the Rat After the Administration of the Aminonucleoside of Puromycin" by K.P.G. Harris, J.B. Lefkowith, S. Klair and G.F. Schreiner, *J. Clin. Invest.,* vol. 86, Oct. 1990, pp. 1115–1123.

"Essential Fatty Acid Deficiency Prevents Multiple Low–Dose Streptozotocin–Induced Diabetes in CD–1 Mice", by James R. Wright, Jr., James B. Lefkowith, George Schreiner and Paul E. Lacy, *Proc. Nat'l Acad. Sci., U.S.A.,* vol. 85, Aug. 1988, pp. 6137–6141.

"Macrophage–Specific Chemotacitc Lipid Release by in Vivo Streptozocin–Administered Mouse Islets" by Andrew Muir, Brad H. Rovin, Paul E. Lacy, and George Schreiner, *Diabetes,* vol. 40, Nov. 1991, pp. 1459–1466.

"The Ratio of Trienoic: Tetraenoic Acids in Tissue Lipids as a Measure of Essential Fatty Acid Requirement" by Ralph T. Holman, *J. Nutrition, 70* (1960) pp. 405–410.

"Reduced Exudation and Increased Tissue Proliferaton During Chronic Inflammation in Rats Deprived of Endogenous Prostagland in Precursors", by I.L. Bonta, M.J. Parnham and M.J.P. Adolfs, *Prostaglandins,* vol. 14, No. 2 , Aug. 1977, pp. 295–307.

"Chemotaxis and Methylation in a Macrophage Cell Line" by Robert R. Aksamit, and Peter S. Backlund, Jr., *Surv. Immunol. Res.*vol. 2, (1983) pp. 150–154.

"A 48–Well Micro Chemotaxis Assembly for Rapid and Accurate Measurement of Leukocyte Migration" by Werner Falk, Richard H. Goodwin, Jr., and Edward J. Leonard, *Journal of Immunological Methods,* vol. 33 (1980), pp. 239–247.

"Raspailynes, Novel Long–Chain Acetylenic Enol Ethers of Glycerol from the Marine Sponges *Raspailia pumila* and *Raspailia ramosa*" by G. Guella et al. *Heveltica Chimica Acta.* 70: 1050–1062 (1987).

Chem. abstr., Bacon et al., 114:99349., 1991.

MACROPHAGE LIPID CHEMOATTRACTANT

This application is a divisional of application Ser. No. 08/470,974 filed Jun. 6, 1995, which in turn is now U.S. Pat. No. 5,663,450, and a continuation-in-part of U.S. patent application Ser. No. 08/107,958 filed Aug. 17, 1993, now abandoned.

BACKGROUND OF THE INVENTION

1. Field of The Invention

This invention is in the field of chemotaxis and chronic inflammation.

2. Related Prior Art

The effector cell of chronic inflammation is the macrophage. The macrophage in inflamed tissues is derived from circulating monocytes that originate in the bone marrow. In response to signals from injured tissue, as yet incompletely understood, the monocyte binds to and then migrates beneath the endothelium lining the vascular structures through which it is circulating. Once in a subendothelial position, the monocyte activates and differentiates into a macrophage. The activated macrophage releases a variety of factors that degrade extracellular matrix, stimulate collagen production, and promote proliferation of endothelial cells, fibroblasts, and vascular smooth muscle cells. These factors include proteases, reactive oxygen species, and cytokines such as interleukin-1, tumor necrosis factor, and platelet-derived growth factors, among others, Nathan, C. F. 1987. *J. Clin. Invest.* 79: 319–326. The end result is the promotion of wound healing or, in the case of inflammation occurring within a bodily organ, cell proliferation and sclerosis that may eventuate in impairment of organ function. Thus the macrophage is central to the pathological processes underlying myocardial fibrosis, atherosclerosis, restenosis, pulmonary fibrosis, progressive nephrosclerosis, arthritis, and inflammatory bowel disease, to cite a few examples of chronic inflammatory conditions, Kissane, J. ed. *Anderson's Pathology,* 1990. C. V. Mosby, St. Louis, Mo. pp. 89–96, 615–730, 804–871, 920–1047, 1153–1199, 2065–2105.

There are two components of monocyte movement into tissues. The first component consists of monocyte adhesion to the endothelium. There is a growing literature on the expression of adhesion proteins by endothelial and other cells that promote the binding of leukocytes, including monocytes, to the endothelium, Springer, T. 1990. *Nature,* 346: 425–433. The second component is the signal for chemotaxis, the signal released by traumatized tissue that induces migration of the monocyte beyond the endothelial cell to which it is adhering and into the tissue underlying the endothelium.

The factors regulating the subendothelial migration of monocytes into tissue in normal and inflammatory states are not well understood. Like neutrophils, monocytes display chemotactic migration to C5a, the bacterial tripeptide f-Met-Leu-Phe, proteolytic fragments of collagen and fibronectin, platelet-derived growth factor, transforming growth factor-β, and neuropeptides. Schiffman, E., & Gallin, J. 1979. *Curr. Top Cell Reg.* 15: 203–213; Pierce, G., et al 1989. *J. Cell Biol.* 109: 429; Snyderman, R., & Mergenhagen S. 1976. In *Immunobiology of the Macrophage* pp. 323–348, New York Academic Press.

The contribution of the factors cited above to maintaining the mononuclear leukocytic invasion of chronically inflamed tissues has not been defined. Since these factors attract both neutrophils and monocyte/macrophages, and because neutrophils are not a prominent component of chronic inflammatory lesions, there is continuing interest in further identifying chemotactic signals unique to the monocyte or macrophage. The identification of such a chemotactic agent should meet three criteria: 1) it should be chemotactic for monocytes but not neutrophils in vitro; 2) it should be identified in lesions associated with chronic infiltration by monocytes/macrophages; and 3) interruption of its synthesis, release, or receptor activation should be associated with amelioration of chronic inflammation in vivo.

There is only one known chemotactic signal, a protein, unique to the monocyte. It is a lymphocyte-derived, 8 kD, chemotactic protein known as macrophage chemotactic protein, which has been sequenced, Furutani, Y., et al 1989. *Biochim. Biophys. Res. Comm.* 159: 249. However, no in vivo inhibition of its function has been achieved to date to confirm its role in macrophage migration in vivo.

It has become evident that altered lipid metabolism, particularly hyperlipidemia, may induce or augment monocyte migration into the walls of vascular tissue. The early phase of atherosclerosis is characterized by subendothelial migration of monocytes in the aorta and coronary arteries, Ross, R. 1986. *N. Eng. J. Med* 296: 488. Hyperlipidemia accelerates the renal infiltration by monocytes in chronic inflammation of the glomerulus and interstitium, Diamond, J., & Karnovsky, M. 1988. *Kid. Int.* 33: 917. Although there is a clear association between lipidemia and monocyte migration into extravascular spaces, no lipid chemotactic factors have been described that are specific for monocytes at physiological concentrations. $LTB_4$ is highly chemotactic for polymorphonuclear leukocytes (PMN), much less so for human monocytes, and not all for mouse or rat monocytes, Kreisle, R., et al 1985. *J. Immunol.* 134: 3356. Platelet activating factor is minimally chemotactic for rat monocytes and more stimulatory for neutrophils, Goetzl, E., et al 1980. *Biochim. Biophys. Res. Comm.* 94: 881; Rovin, B., et al *J. Immunol.* A lipid generated during oxidative modification of lipoprotein, lysophosphatidyl choline, possesses modest chemotactic properties for human monocytes, Quinn, M., et al 1988. *Proc. Natl. Acad. Sci.* 85: 2805, but at extremely high concentrations not found in nature.

To date, there has been no demonstration that in vivo inhibition of chemotactic factors specifically interrupts monocyte migration into tissues. This is true for both the macrophage chemotactic protein as well as for lipid mediators of inflammation.

The model that we have most commonly employed for the study of monocyte chemotaxis in vivo is nephrotoxic serum nephritis, in which rats receive an injection of rabbit anti-glomerular membrane (GBM) antibody. Polymorphonuclear leukocytes (PMNs) enter the glomerulus in the first 3 hours followed by monocytes at 12–24 hours. Schreiner, G., et al 1978. *J. Exp. Med.* 147: 369. It has been shown that infiltration is not dependent upon complement activation. Schreiner, G., et al 1984, *Lab. Invest.* 51: 524.

The role of essential fatty acid (EFA) deficiency on the renal infiltration by monocytes of these cells has been studied. Hurd, E., et. al. 1981. *J. Clin. Invest.* 67: 476, found that NZB/NZW F1 mice with systemic lupus erythematosus did not die of renal failure if placed on a diet deficient in the essential fatty acids, linoleate and arachidonate, despite documented deposits of immune complexes in their glomeruli, and circulating immune complexes. Subsequently it was shown that EFA-deficiency resulted in a marked reduction in the number of resident renal glomerular and interstitial macrophages Lefkowith, J., & Schreiner, G.

1987. *J. Clin. Invest.* 80: 947. When animals were selectively repleted with (N-6) fatty acid supplementation, it was observed that a spontaneous macrophage repopulation of the glomerulus occurred. It had been previously shown that resident macrophages in the kidney expressing the Ia+ antigene are highly stimulatory in a mixed lymphocyte culture reaction. The effect of whether depletion of these cells from the kidney via this dietary manipulation would decrease the immunogenicity of the kidney when transplanted across a major histocompatibility barrier was studied. Kidneys harvested from a Lewis EFAD donor and transplanted into a Buffalo strain rat on a normal diet survived as allografts in the absence of immunosuppression of the recipient Schreiner, G., et al 1988. *Science* 240: 1032. Allografts from EFAD donors normalized their lipid composition within the allogeneic recipient and were repopulated with host macrophages within 5 days. The rapid repopulation of the kidney with host macrophages closely paralleled the restoration of the essential fatty acid content of nospholipids, suggesting that the seeding of organs by macrophages could be dependent in part upon a lipid pathway.

The potential role of this lipid pathway in mediating the inflammatory influx of macrophages into the kidney, in acute nephrotoxic nephritis, has been evaluated Schreiner, G., et al 1989. *J. Immunol.* 143: 3192. The effects of EFA-deficiency were striking. EFA-deficiency completely prevented the influx of macrophages into the glomerulus during the course of the nephritis. In contrast, the preceding PMN influx was unaffected. EFA-deficiency completely prevented polyuria, azotemia, and sodium retention, and largely abrogated the proteinuria. EFA-deficient macrophages are not impaired in their ability to move chemotactically toward either C5a or platelet activating factor; and no circulating inhibitors of chemotaxis were found in EFA-deficient serum, suggesting the effect of EFA-deficiency may be exerted at the level of tissue-derived factors inducing monocyte migration Schreiner, G., et al 1989. *J. Immunol.* 143: 3192; Rovin, B., et al 1990. *J. Immunol* 145:1238.

Using our dietary model, Diamond, J., et al 1989. *Am. J. Physiol.* 257: F798, discovered that animals deficient in essential fatty acids, deficient only during the period of acutely induced nephrotic state by PAN, were protected against the development of glomerular sclerosis four months later. The protection against glomerular sclerosis did not correlate with the degree of proteinuria, hyperlipidemia, or hypertension. Rather, it directly correlated with the inhibition of glomerular macrophage accumulation normally induced by the hyperlipemic state of nephrosis.

It has been observed that EFA-deficiency also prevents the renal mononuclear cell interstitial infiltrate of acute PAN-induced nephrosis and reverses the profound decrease in renal blood flow normally observed in the acute phase of this disease. Parallel experiments with marrow irradiation demonstrated that the predominant effect of EFA-deficiency on preserving renal blood flow and glomerular filtration could be attributed to on blocking mononuclear migration into the interstitium, Harris, K., et al 1990. *J. Clin. Invest.* 86: 1115.

Importantly, this effect is not confined to the kidney. EFA-deficiency inhibits the development of autoimmune insulitis in mice receiving low dose streptozotocin and in the diabetes-prone BB/Wor rate, Wright, J., et al 1988. *Proc. Natl. Acad. Sci.* 85: 6137; Lefkowith, J., et al 1989. *J. Exp. Med.* 161: 729. Both are models of diabetes in which insulitis is preceded by islet infiltration by monocytes. It has been demonstrated that pancreatic islets undergoing oxidative stress after in vivo exposure to streptozotocin release an uncharacterized lipid chemoattractant, specific for monocytes, resembling from that released by isolated glomeruli, Muir, A., et al 1991. *Diabetes* 40: 1459. In skin graft experiments, we have observed impaired wound healing in fatty acid deficient animals with marked inhibition of monocyte accumulation in the traumatized skin and inhibited formation of granulation tissue (unpublished observations). EFA-deficiency has previously been shown to protect against atherosclerosis, Holman, R. T. 1960. *J. Nuir.* 70: 405, and inhibit carrageenan-granuloma formation, Bonta, F., et al 1977. *Prostaglandins* 14: 295, and diminish the leukocyte inflammation associated with experimental myocardial infarction.

The release of a potent uncharacterized chemoattractant for monocytes, Rovin, B., et al 1990. *J. Immunol* 145: 1238, has been described in short-term cultures of nephritic glomeruli from rats on a standard diet. Production of this chemoattractant is markedly enhanced after induction of nephritis. EFA-deficient nephritic glomeruli do not release the monocyte chemoattractant. In vivo studies employing inhibitors of cyclooxygenase and lipoxygenase have demonstrated that this chemoattractant is not a product of either pathway. Administration of a platelet activating factor (PAF) receptor antagonist similarly failed to inhibit the glomerular influx of macrophage. Lipid (Blight-Dyer) extraction of nephritic glomeruli from control diet animals has yielded chemoattractant activity in the organic phase, Rovin, B., et al 1990. *J. Immunol* 145: 1238.

These findings suggest that a lipid pathway, metabolically linked to dietary fatty acids, may provide a generalized mechanism for the induction of monocyte infiltration into tissues.

An article by Graziano Guella et al., *Helvetica Chimica. Acta.* 70; 1050–1059 (1987) describes various long chain acetylenic enol ethers of glycerol derived from marine sponges. The compounds identified, however, are not the same as the lipid chemoattractant of this invention because the compounds described in Guella et al. have properties inconsistent with the properties of the compound of this invention. Specifically, the activity of the Guella et al. compounds, if any, would not be inhibited by selective reducing agents as sodium borohydride. Likewise, the compounds of Guella et al., which are ethers of marine sponges, have never been isolated and purified from urine or plasma of mammals including humans. Furthermore, unlike the lipid chemoattractant of this invention, the Guella et al. compounds would not lose their activity, if they exhibit any, at temperatures in excess of 180° C. Finally, the Guella et al. compounds include conjugated double bonds which exhibit a characteristic UV absorption ($\lambda_{max}$) of 292. The lipid chemoattractant of this invention does not exhibit UV absorption at 292, indicating that the double bonds are not conjugated.

SUMMARY OF THE INVENTION

This invention encompasses a substantially homogeneous lipid chemoattractant released from stressed mammalian tissue which is a neutral lipid which is acid labile and stable to base and is stable in boiling water. This lipid recruits macrophages but not neutrophils to stressed tissue. The invention further encompasses a method for detecting injured tissue by detecting the presence of the above described lipid chemoattractant in body fluids such as urine, serum and saliva. The invention also includes a method for reducing recruitment of macrophage to injured tissue by reducing the amount of the above lipid chemoattractant or by blocking the interaction of this lipid chemoattractant with monocyte/macrophage binding sites. The addition of this lipid chemoattractant to injured skin tissue promotes healing.

A purification scheme has been devised that results in the chromatographic isolation of an almost homogeneous neutral lipid that constitutes the newly described factor of chronic inflammation of this invention. The purification scheme includes extracting a crude organically extracted medium containing the lipid chemoattractant and contaminants from a mammalian source. The extract is separated by silica-based separation techniques to give a first separation product comprising the lipid chemoattractant and at least one fatty acid contaminant. The separation product is hydrolyzed with an alkaline agent to give a hydrolyzed product comprising the lipid chemoattractant and cleaved fatty acid contaminants. Finally, the hydrolyzed product is separated using silica-based separation techniques to give an essentially pure solution of the lipid chemoattractant.

The isolated compound does not resemble any previously described lipid inflammatory factor. It specifically induces the chemotactic migration of monocytes into extravascular tissues. It has been isolated from both animal and human examples of organ disease associated with the accumulation of monocytes/macrophages on a persistent basis. It has been shown to be associated with the following conditions: glomerulonephritis, nephrosclerosis, interstitial nephritis, nephrosis, and diabetes. The factor is inferentially associated with atherosclerosis, pneumonitis, pulmonary fibrosis, myocardial infarction and fibrosis, and chronic dermatitis.

The factor itself resembles, based on its chemical properties, a monoglyceride with a vinyl ether linkage. As an agonist it could be used as an aid to wound healing. Antagonism of this factor could be expected to suppress chronic inflammation of the lungs, heart, blood vessels, pancreas, kidney, peripheral vasculature and the kidney.

Detection of this material has occurred in the urine and peritoneal fluid of patients with a variety of chronic kidney diseases. Detection of this factor is a useful diagnostic or prognostic assay in the urine, blood, peritoneal fluids, or stool of patients with myocarditis, myocardial infarction, pneumonitis, pulmonary fibrosis, glomerulonephritis, interstitial nephritis, nephrosis, progressive renal insufficiency, atherosclerosis peripheral vascular disease, chronic dermatitis or inflammatory bowel disease. The use of a blood diagnostic assay may be of particular utility in the diagnosis and/or management of atherosclerosis.

DETAILED DESCRIPTION OF THE INVENTION

Figure 1:
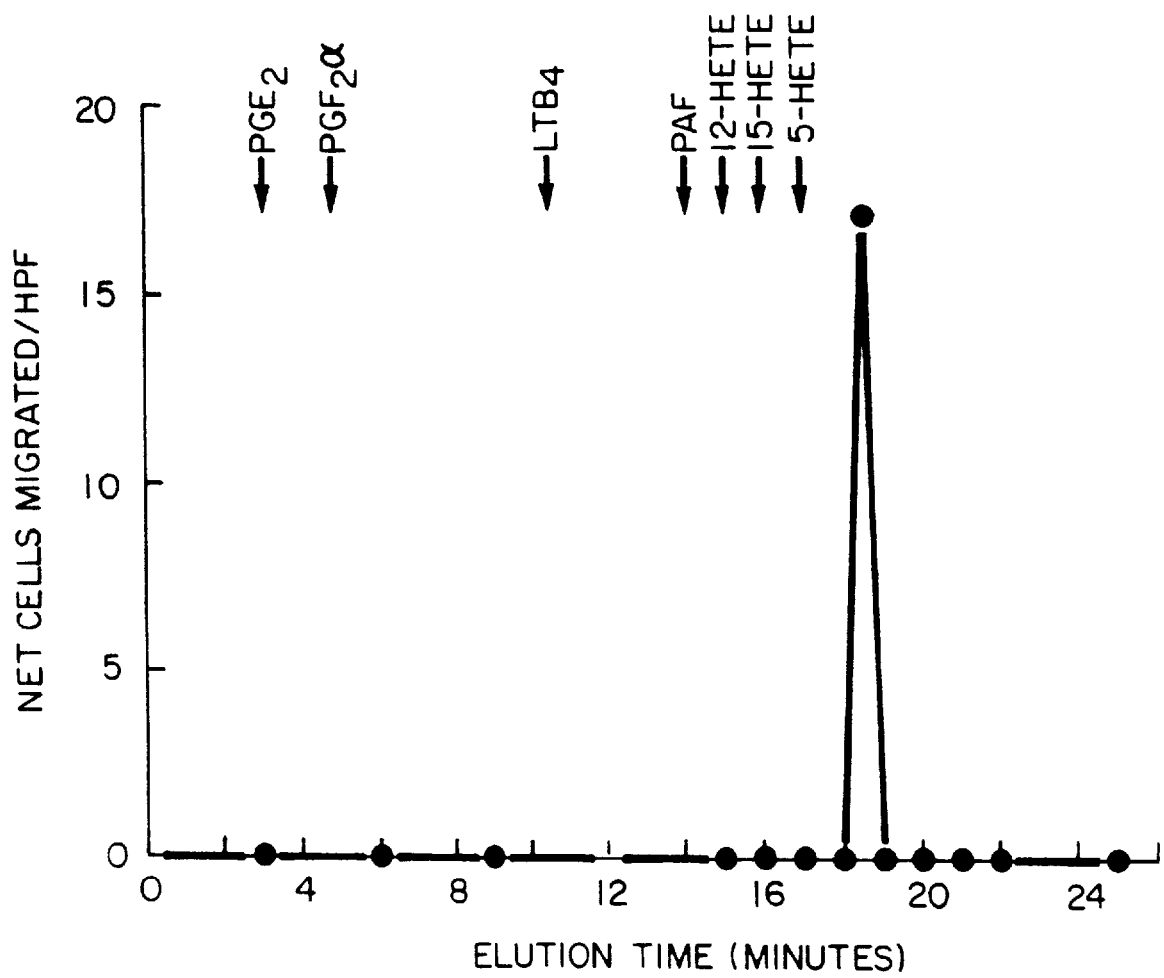
FIG. 1. HPLC chromatographic isolation of a peak of chemotactic activity isolated from inflamed renal glomeruli. The activity is designated as inducing cell migration, expressed as cells (monocytes)/HPF.

This invention is a purified lipid chemoattractant derived from stressed mammalian cells as well as a method for purifying the lipid chemoattractant. Furthermore, this invention includes inhibitors of the lipid chemoattractant as well as inhibitors of monocyte chemotaxis.

The purified lipid chemoattractant of this invention is useful for developing methods and agents for detecting the lipid chemoattractant in stressed mammalian cells. The purified agent is also useful for developing and identifying inhibitors of the agent as well as inhibitors of monocyte chemotaxis, the physiological mechanism that produces the agent. The purified lipid chemoattractant of this invention can also be used topically or internally to promote wound healing.

The isolation and purification of the lipid chemoattractant of this invention has permitted us to study and characterize the agent based on it chemical and biological characteristics as well as its structure. Our understanding of the chemical structure of the lipid chemoattractant of this invention is based on a number of types of studies performed on the agent including refining and improving methods for purifying the agent, characterizing biochemical properties of the agent, characterizing the metabolic pathway to synthesis of the agent, identifying inhibitors to the synthesis of the agent, by identifying inhibitors of monocyte chemotaxes and by preparing synthetic analogs of the agent. None of these characterization efforts nor the identification of inhibitions would have been possible without first having a substantially homogeneous form of the lipid chemoattractant to work with.

A purification method that reproducibly yields a substantially homogeneous monocyte chemotactic factor released by glomeruli or renal interstitium has also been developed. Previous attempts at characterizing this factor were difficult because isolated fractions possessing biological activity were extremely heterogeneous and insufficient purity precluded biochemical definition of the lipid chemoattractant.

The identification of this novel factor as a neutral lipid and its unusual stability to alkaline methanol has allowed further refinement in its isolation such that we can prepare the lipid factor, with potent chemotactic activity, with minimal contamination by other lipids from both tissue conditioned medium and bodily fluids such as urine. Unpurified sources of the lipid chemoattractant include, but are not limited to the mouse monocyte leukemia line, RAW 264.7 is used as an indicator. The cell line is distinctive for its normal responsiveness to physiological concentrations of macrophage activation signals, including endotoxin and gamma interferon. These cells have been used as a model system for evaluating monocyte chemotaxis. These cells are periodically compared to glycogen-elicited rat peritoneal macrophage to assure their reliability.

In a standard protocol for eliciting the release of a chemotactic factor, rats are injected with rabbit anti-rat glomerular basement membrane antibody. Control rats received rabbit immunoglobulin prepared from non-immune serum. The glomeruli are harvested 12 hrs. later after saline-perfusion of the kidney and cultured in RPMI 1640 with 10 mM HEPES and 0.25% fatty acid free albumin.

After 2 hours, the glomeruli and medium are extracted by the method of Bligh and Dyer or, in a preferred step, with ethyl acetate. Aliquots tested in micro chemotaxis chambers, according to the method of Falk, Falk, W., et al 1980. *J. Immunol. Meth.* 33: 239, demonstrate chemotactic activity as measured by the enumeration of cells migrating through filters. Parallel extractions of normal glomeruli and EFA-deficient glomeruli yield no activity.

We have identified numerous physical, chemical, and biological properties for this novel neutral lipid macrophage chemoattractant.

Figure 2:
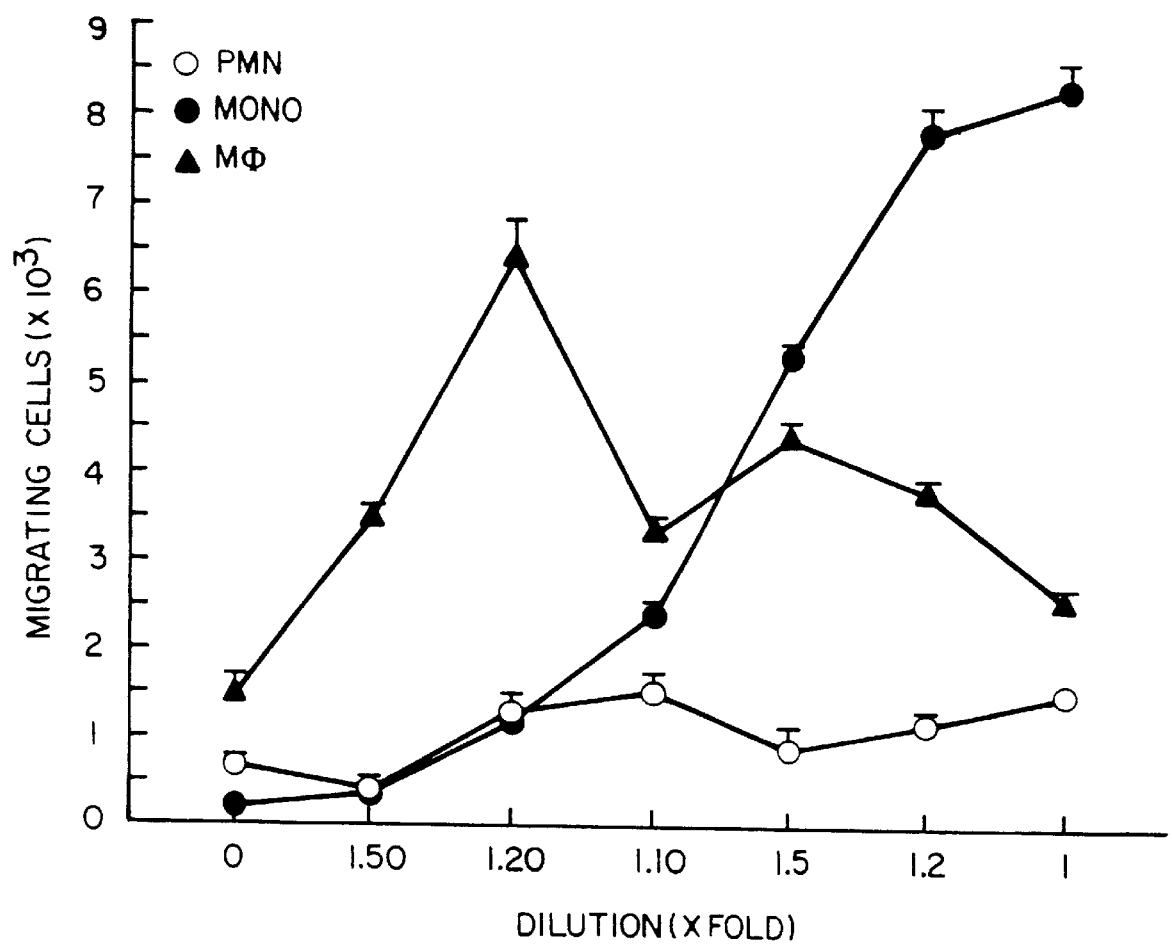
FIG. 2. The chemotactic response of neutrophils monocytes, and macrophages to chromatographically purified lipid chemoattractant.

The factor is insensitive to trypsin, pronase, or collagenase. Inhibitors of cyclo-oxygenase and lipoxygenase activity exert no effect on the generation of the chemo lipid in vivo or in vitro, but conditions favoring oxidation increase its activity. It is not inactivated by heating up to 100° C. for five minutes. It cannot be modified by diazomethane indicating the lack of a free carboxy group. The factor can be sililated with trimethylsililate (BSTSMFA), delaying its elution on HPLC, with recovery of biological activity after hydrolysis in an aqueous medium. This suggests the presence of free hydroxyl or amino groups. It is extracted into ethyl acetate and migrates as a neutral lipid by TLC and HPLC chromatographic techniques. Exposing the material to 0.5 N KOH in methanol results in no loss of chemotactic activity. However, subjecting the material to 0.5 N HCL in methanol for 30 minutes effected virtually complete loss of detectable chemotactic activity as did exposure to concentrated HCL fumes, indicating that the biological active molecule has a vinyl ether or similarly acid labile linkage, and that an ester bond is not necessary for biological activity. Lipid phosphorus is not detected on either the TLC fraction or the active HPLC fractions either by phosphomolybdate spray (TLC) or by ashing (HPLC/TLC) and assaying by the method of Rouse et al., Rouse, R., Fleischman, B., and Yamamoto, F. 1970. *Lipids* 49: 497. It is sensitive to reduction by vitride or sodium borohydride. This factor has no chemotactic activity for polymorphonuclear leukocytes (FIG. 2). According to all thin layer and column-based chromatographic analyses, the lipid chemoattractant of this invention is a short-chain (n(12) monoalkyl glycerol or an oxidized long-chain (n)16) monoalkylglycerol. In summary, its chromatographic properties as an acid sensitive, nonpolar lipid with no effect on neutrophils distinguishes it from platelet activating factor and $LTB_4$ (FIG. 1), the only other defined lipid macrophage chemotactic factors, and identify the isolated factor as novel.

It has been demonstrated that the proximal tubules are a source of the chemotactic lipid by isolating proximal tubules by density sedimentation of renal cortical digests from albumin-injected rats. When proximal tubules were placed in overnight culture, lipid extracts of harvested supernatants demonstrated release of considerable chemotactic activity. The elution characteristics on HPLC were identical to those described above. On the other hand, extracts of supernatant from the culture proximal tubules from control rats were inactive.

Figure 3:
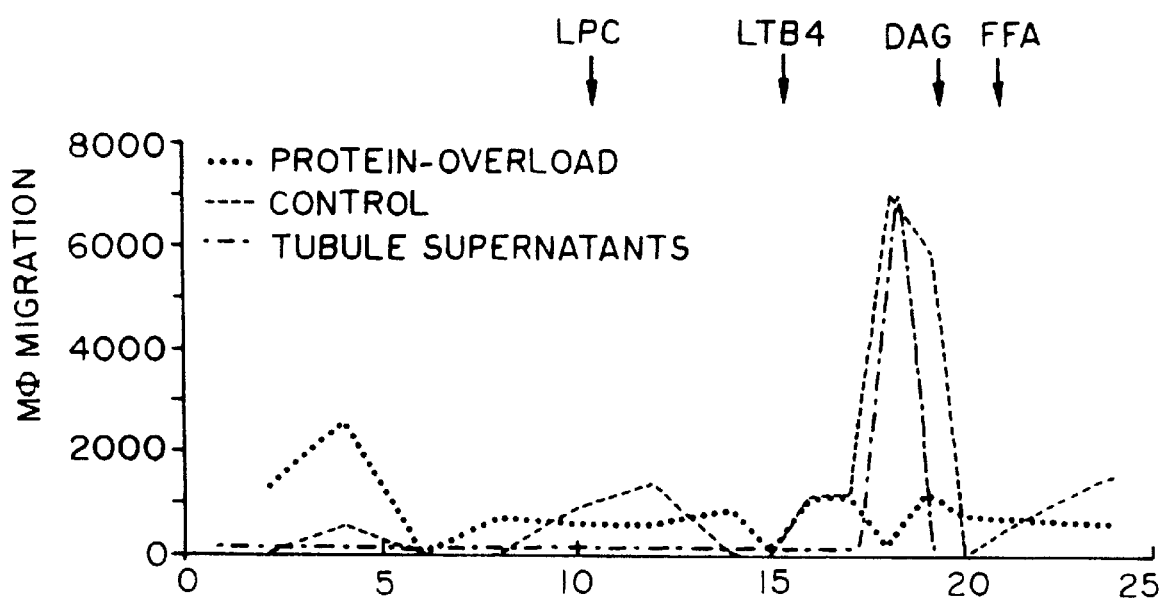
FIG. 3. HPLC chromatographic isolation of a peak of chemotactic activity isolated from supernatants fed albumin replete with fatty acids, no albumin (control) and urine from animals rendered proteinuric by administration of 1 gram albumin intraperitoneally for 5 days.
Figure 4:
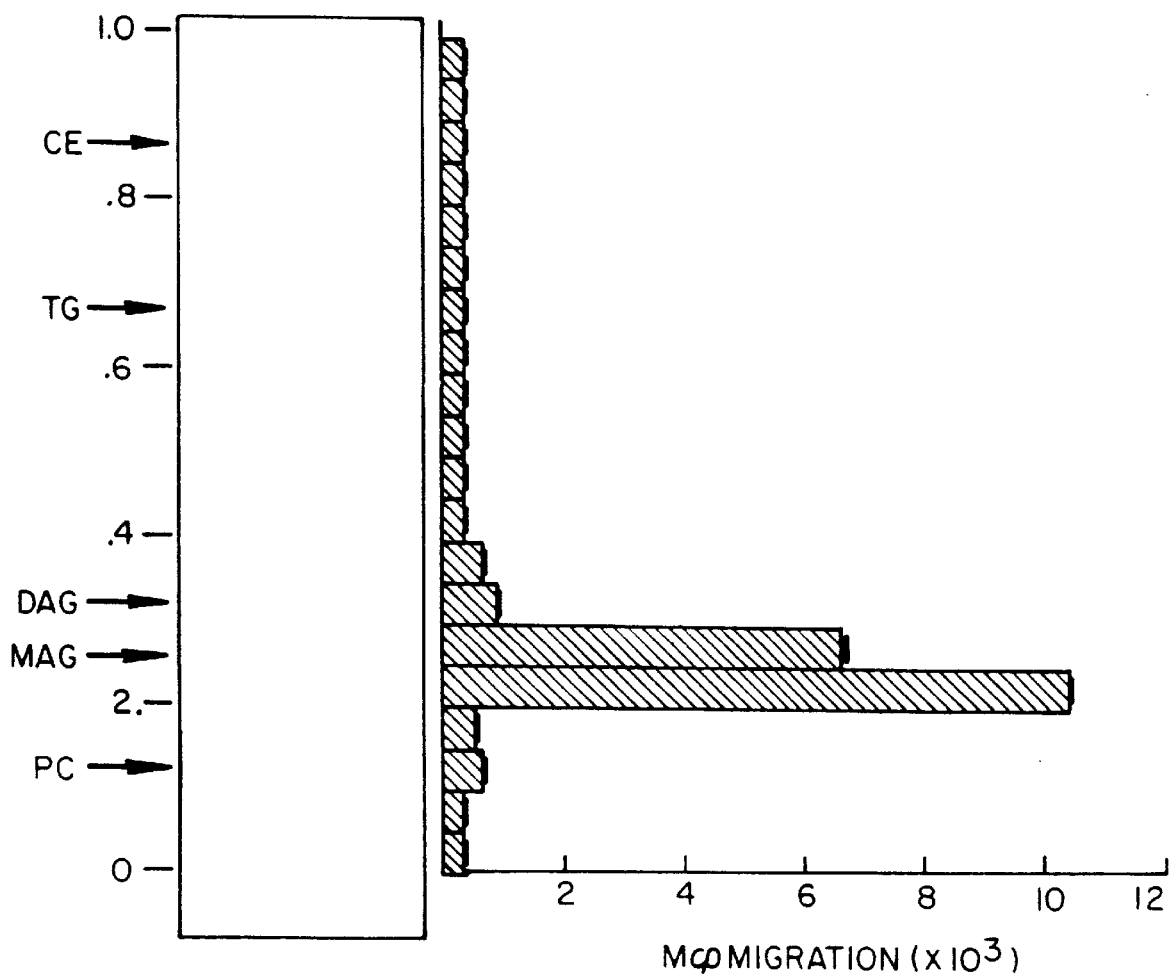
FIG. 4. Comigration of lipid chemoattractant with monocylglycerols, as isolated from medium of proximal tubules fed albumin oleate.
Figure 5:
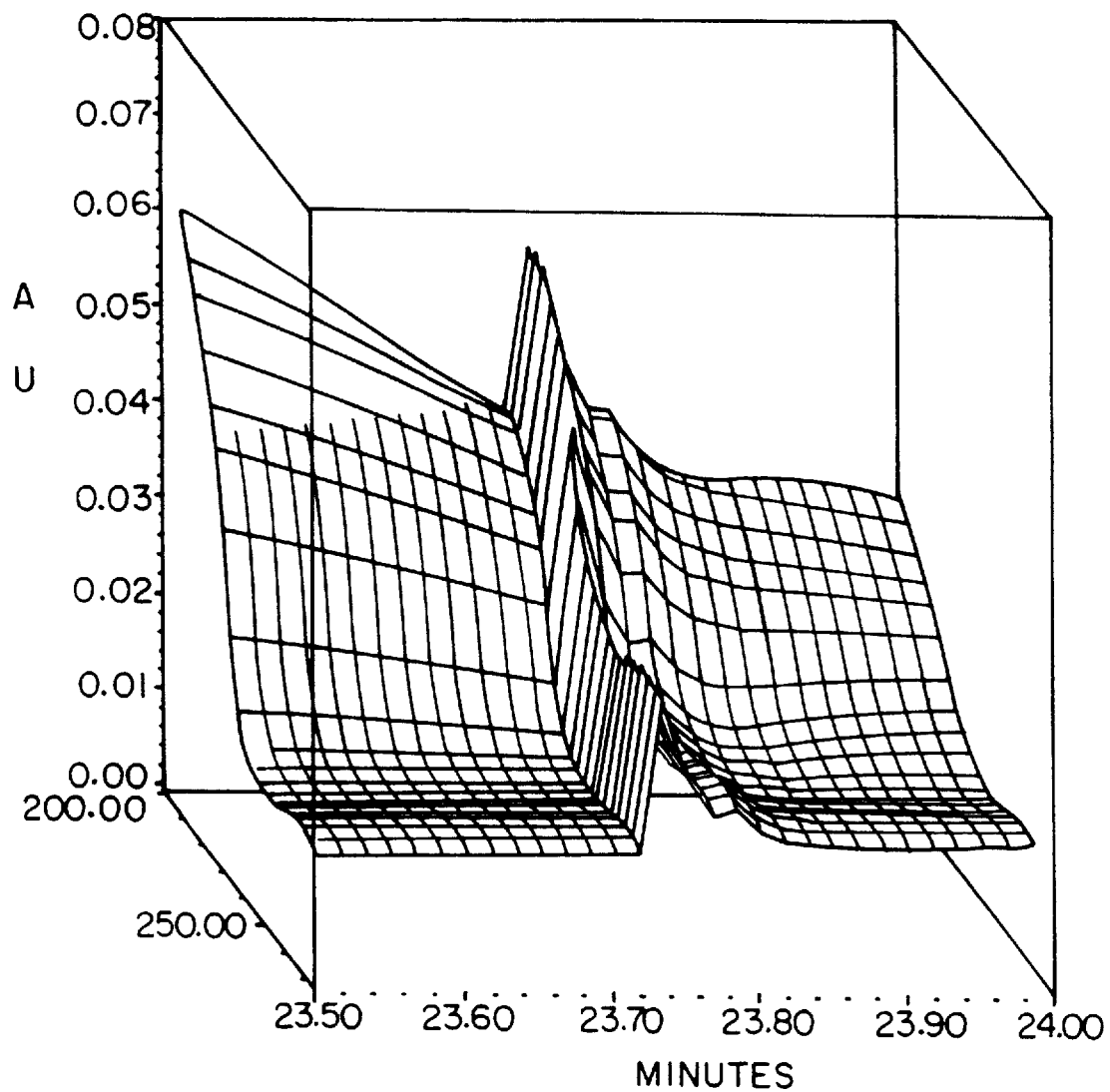
FIG. 5. HPLC isolation of a single peak of lipid (as determined by UV absorption scan between 200 and 250 nM) possessing chemotactic activity.

Chemoattractant activity can be stimulated in proximal tubules from normal rats placed in overnight culture in medium containing 5 mg/ml of lipid replete bovine serum albumin (BSA). Supernatant from the tubules cultured in the presence of lipid-replete albumin contained chemotactic activity similar in magnitude to that seen in the supernatants of tubules from the protein overloaded animals. However, the supernatants from the tubules cultures in the presence of lipid-depleted albumin contained little activity. The isolated activity from the lipid-repleted BSA supernatants showed mobility identical to that of the activity in the urine of proteinuric rats on TLC. The elution profile of chemotactic activity recovered from proximal tubules on HPLC was superimposable on that observed in the urine of proteinuric animals. (FIG. 3) Feeding the proximal tubules albumin that has been selectively loaded with individual fatty acids has demonstrated that oleate and the myristate are the most stimulatory fatty acids.

Figure 6:
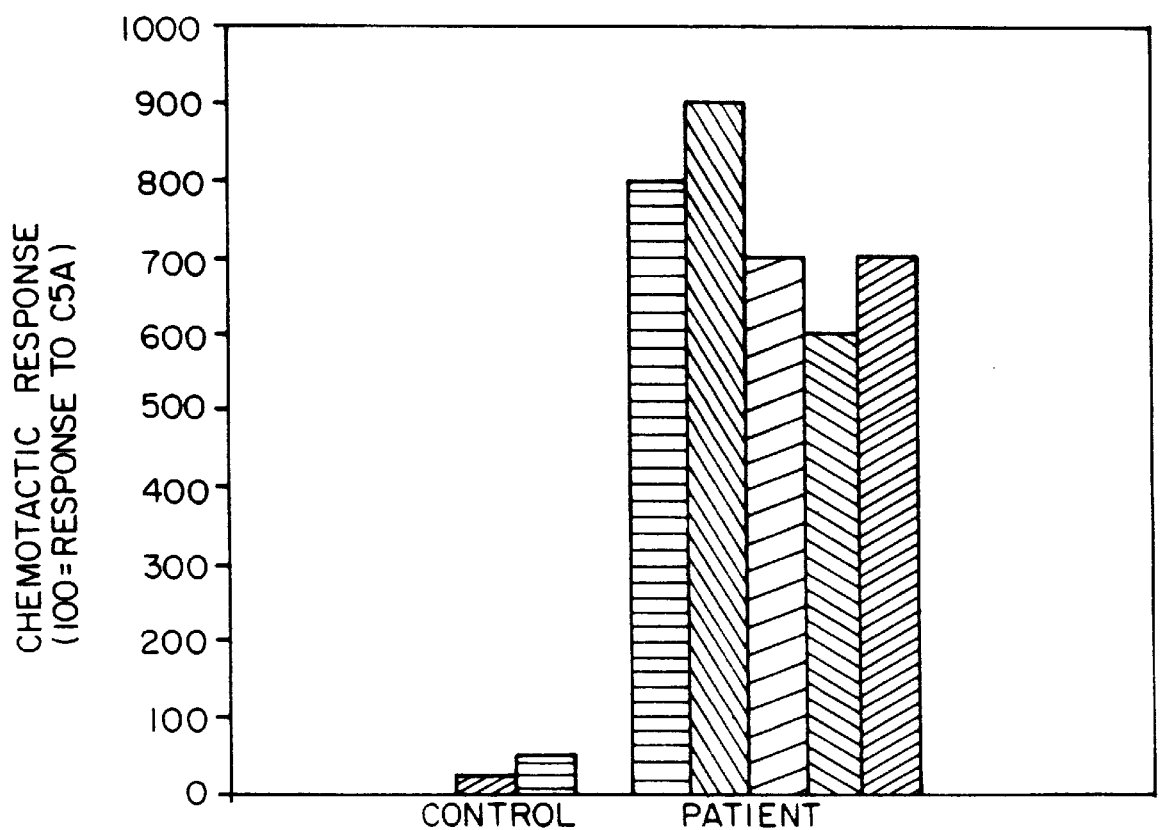
FIG. 6. Plot indicating the presence of lipid chemoattractant in plasma of humans suffering from atherosclerosis, ("PATIENT"), and the relative absence of the lipid chemoattractant in the plasma of healthy humans, ("CONTROL").

Using the system of extraction into ethyl acetate, separation by TLC and purification by reverse phase HPLC as described in Examples I and II below, we have identified a molecule with identical chromatographic properties in the urine of patients with proteinuric kidney disease. We have also identified the molecule in the plasma of humans with atherosclerosis and the relative absence of the molecule in patients without the condition (FIG. 6). Conditions in which high levels of this lipid chemoattractant has been identified include diabetes, membranous nephropathy, focal segmented sclerosis and glomerulonephritis. Two patients with proteinuria and stable renal function have control levels of this agent. These data indicate that the presence of this material in urine and other fluids has diagnostic and prognostic utility for detecting tissue injury such as the kidney. (Table I).

The lipid chemoattractant is detected mammalian tissues and serum sources by subjecting the tissues and serum or any other potential source of lipid chemoattractant to the purification methods described in Examples II and III. The resulting pooled product then undergoes standard bioassay testing to determine whether or not the lipid chemoattractant is present and also to determine the amount present.

The lipid chemoattractant has additional distinctive attributes. It is not sequence or species specific. The same factor, as defined by chromatographic characteristics and biological activity, has been isolated from humans, rats, and mice. Monocytes from any of these species are equally responsive to the factor regardless of the species from which it is isolated. Cells or organs known to produce this factor include vascular smooth muscle cells, pancreatic islets, renal glomeruli, renal proximal tubular epithelium, and intact aortas. Signals or stresses that we have shown to promote release of this factor include uptake of lipoproteins, including albumin, intracellular oxidation, anoxia, tissue culture, immune complexes, and mechanical stretch of luminal structures, as is seen in obstruction of hypertension.

TABLE I

| Monocyte CTX Activity in Extracted, Chromoatographed Urine (18'–20') | |
|---|---|
| | MONOCYTE MIGRATION (cells/filter) |
| PROGRESSIVE RENAL DISEASE | |
| FSGS | 11,039 |
| FSGS | 23,140 |
| IgA/TIN | 24,386 |
| Diabetes | 21,184 |
| STABLE RENAL FUNCTION | |
| Control | 2,492 |
| FSGS (obese) | 2,552 |
| FSGS (non-progressive) | 2,492 |

The identification of the lipid chemotaxis factor as a vinyl ether monoalkyl glycerol has permitted the design of inhibitors. A variety of naturally occurring fatty acids were screened for the capacity to inhibit the oleate stimulation of the novel lipid chemoattractant.

Inhibitors of the synthesis of the lipid chemotaxis factor include long chain polyunsaturated fatty acids and particularly C18:3, C:20:3, and C:20:5 fatty acids. C18 fatty acids with substitutions between $C_6$–$C_{12}$, e.g., ricinoleate, are also inhibitory. The most inhibitory fatty acids reflect modifications of fatty acids between the C9 and the omega carbon. In order of potency, the fatty acid inhibitors are: ricinoleic acid>eicosopentanoic acid>mead acid>docosohexanoic acid>linolenate>eicosadienoic acid. Ricinoleic acid is 100% inhibitory at micromolar concentrations.

Ethanol is inhibitory as are lipid soluble antioxidants such as ethoxyquin, butylated hydroxytoluene, and butylated hydroxyanisole. Cytrochromic $P_{450}$ enzyme inhibitors such as ketoconazole and clotrimazole are also inhibitors of the synthesis of the lipid chemoattractant as are alcohols of long chain fatty acids.

A prototype receptor antagonist has been synthesized from commercially available beef heart phosphotidylcholine, which contains 30% plasmalogens (Sigma Chemical Co., St. Louis, Mo.). The phosphotidylcholine/plasmalogen mixture was subjected to phospholipase C exposure followed by alkaline hydrolysis in 0.5 NaOH in methanol and TLC separation. This yielded a mono-alkyl vinyl ether of glycerol, which was labile in 0.5 N HCl. Its two principal substituents at the SN-1 position were the corresponding vinyl ether derivatives of palmitate and oleate. This mixture had no intrinsic chemoattractant agonist activity. However, at $10^{-6}$ M concentrations, it completely blocked monocyte migration in vitro to biologically active fractions prepared from chromatographic isolates from proteinuric urine. This demonstrates that monoglycerides with long chain fatty acid-derived substituents linked as vinyl ethers in the Sn-1 position of glycerol inhibit the leukocyte response to biologically active mono-alkyl glycerides.

Other monocytechemoxis inhibitors include inhibitors lysomal acidification such as chloroquine and ammonium chloride.

Thus the lipid chemoattractant of this invention has the general structure I:

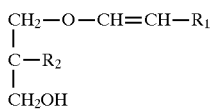

where $R_1$ is a C4–C22 alkyl group optionally containing 1–3 branched group. Each branched group may be a hydroxyl group, oxygen, or a carbonyl group. $R_1$ may include 1–3 unsaturated double or triple bonds but $R_1$ is unconjugated so none of the double can share adjacent carbon atoms.

$R_2$ may be oxygen (O) or HOH. An important aspect of the lipid chemoattractant is that it includes at least one oxygen or carbonyl group. If $R_2$ is oxygen, then $R_1$ may, but need not include a carbonyl group or an oxygen group that is not part of a hydroxyl group. If $R_2$ is HOH, the $R_1$ must include an oxygen that is not part of a hydroxyl group, or carbonyl group as part of the alkyl backbone, or as a branched group.

In addition, those skilled in the pharmaceutical arts will recognize that interfering with the production of I through interference with the pathway that produces I will effectively reduce macrophage migration.

EXAMPLE I

The lipid chemoattractant of this invention has been purified by the following procedure:

Approximately 20–30 ml of urine or medium conditioned by proximal tubules fed albumin complexed with fatty acids are extracted with ethyl acetate (1:1. v/v). After phase separation via centrifugation, the organic phase is collected and subsequently dried using a Buchii rotatory evaporator. The dried samples are stored under argon in a silylated vial.

A 2-step TLC procedure is used to isolate fractions of the extracted urine sample with corresponding chemotactic activity. Samples are spotted on silica gel plate (Whatman LK6DF plate with a pre-absorption zone) and developed initially with a solvent system of chloroform:methanol: acetic acid (60:25:1), v/v/v) to an $R_f$ of 0.3. The plate is dried and then exposed to a second solvent system of petroleum ether: ether: and acetic acid (80:20:1) and developed to an $R_f$ of 1.0. All chemotactic activity elutes from an area comigrating with short and long-chain monoglycerols, $R_f$=0.25±0.05 (FIG. 4), an area which was scraped and eluted with chloroform:methanol (1:1, v/v).

To eliminate contaminating lipid esters which predominate at this point and allow subsequent chromatographic purification to near homogeneity, we utilized the surprising base stability of the lipid chemoattractant to permit substantial enrichment of bioactivity. Thus, the dried eluents are subjected to mild alkaline hydrolysis (0.5N KOH in methanol, at 37° C. for 30 min.). After the completion of the hydrolytic process, the products are extracted with ethyl acetate and separated from the resulting fatty acids with HPTLC (Whatman LHP-KDF with a pre-absorption zone) using a solvent system of petroleum either:ether:isopropanol (3:2:0.6, v/v/v) to an $R_f$ of 1.0 followed by a 5 min over development. The fraction with corresponding chemotactic activity, between $R_f$ 0.4–0.8, is scraped and eluted with chloroform:methanol 1:1, v/v and subjected to further purification using HPLC.

The fraction with chemotactic activity is further purified by HPLC. The sample is loaded onto a Supelco LC-DP diphenyl reversed phase HPLC column (5 u, 25 cm×4.6 mm) with the elution solvent delivered via a Waters liquid chromatograph system equipped with a model 600E controller driven by the Millennium v 1.1 data acquisition and analysis software, and monitored with a Waters model 996 photodiode array detector. A gradient solvent system of acetonitrile (ACN) and water is used to separate the chemoattractant from other contaminants. Initially the solvent system ratio is ACN:$H_2O$ (25%:75%) for 10 min, after which the ACN level is raised to 60% in a duration of 5 min, and to 80% in period of 2 min. Finally, the ACN % was raised to 100% in 10 min. Fractions were collected in 30 second intervals using a Waters fraction collector. All chemotactic activity elutes between 23 and 24 minutes at an ACN % of 92% and the chromatogram shows a single absorbance peak overlapping the chemotactic activity (FIG. 5).

The lipid chemoattractant purified by the method of Example I exhibits the following properties:

TABLE II

Properties of the homogeneous lipid chemoattractant*

| | |
|---|---|
| (a) acid | labile |
| (b) base | stable |
| (c) 100° C. in water | stable |
| (d) macrophages | recruits |
| (e) neutrophils | not-recruited |
| (f) injured tissue | secreted by |
| (g) chemical structure | Sn-1 vinyl ether of glycerol |
| (h) lacks phosphorous | |
| (i) heat lability | activity destroyed 180° C. |

*These properties were demonstrated as follows:
(a) Placed in 0.5N HCl in methanol per 30' at 37° C.
(b) Placed in 0.5N KOH in methanol for 30' at 37° C.
(c) Boiled in $H_2O$ at 100° C. for 15'.
(d) d + e = side by side comparison of the migration of neutrophils (elicited by the installation of zymosan-activated serum in the rat peritoneum) and monocytes (isolated by density sedimentation from the peripheral blood of rats and humans) and macrophages (isolated by instillation of heat-inactivated fetal calf serum in the rat peritoneum).
(h) Lack of phosphorous established by molybdate spray on thin layer chromatograms and by ashing analysis.
(i) Dried to film by evaporation under nitrogen and heated in an oven at 180° C. for thirty minutes.

TABLE III

Chemical Derivatisations Of The Homogeneous Lipid chemoattractant**

| AGENT | STRUCTURAL INDICATION |
|---|---|
| (a) Sodium Borohydride | Carbonyl group<br><br>(R—C—R)<br>\|<br>O |
| (b) Periodate | Adjacent alcohols on adjacent carbonyl alcohol groups.<br><br>R—C—C—R<br>\|   \|<br>OH OH<br><br>or<br><br>C—C—C—R<br>\|   \|<br>OH OH |
| (c) Acetic Anhydride | Alcohol group<br>R--C--OH |
| (d) Acid | Vinyl ether C—O—C=C—C<br>or<br>epoxy group<br><br>    O<br>   / \\<br>C—C———C—C |

**These structural indications were demonstrated as follows:
(a) The lipid chemoattractant is dissolved in ethanol and exposed to solid $NaBH_4$ overnight at room temperature. The material is then reextracted with diethylether in water and tested for biological activity.
(b) Lipid chemoattractant is dissolved in 1% periodate (w/v) in sodium acetate buffer for 1 hour at room temperature after which it is reextracted in ethyl acetate and tested for biological activity.
(c) Lipid chemoattractant is suspended in acetonitrile and exposed to acetic acid anhydride and pyridine for 16 hours at room temperature. Acetylation is reversible by placing acetylated chemoattractant in 0.5 N KOH in methanol for 30 minutes at 37° C.
(d) lipid chemoattractant is placed in 0.5 N HCl in methanol for 30 minutes at room temperature.

All of the above derivitisations destroy biological activity and alter the chromatographic properties of radiolabeled lipid chemoattractant.

EXAMPLE II

This Example describes an improved and alternate method for preparing a essentially homogeneous solution of the lipid chemoattractant of this invention.

The lipid chemoattractant agent is extracted into ethyl acetate from conditioned medium generated from a variety of mammalian sources including human sources such as rat renal proximal tubules or vascular smooth muscle cells or human renal proximal tubules with albumen oleate or lipid containing serum. Other fluid sources of the lipid chemoattractant include plasma, serum, urine, and cyst fluid from human and animal sources. In addition to the lipid chemoattractant, the medium contains impurities and contaminants such as monoalkylglycerols and other low molecular weight compounds (M.W. less than 1000) that do not exhibit biological activity.

The first extract in eluted over a silica column in a mobile phase of petroleum ether:ether (25:75 v/v).

The eluted extract is subjected to alkaline hydrolysis 0.5N KOH in methanol, at 37° C. for thirty minutes and is re-eluted over the silica column in the same manner as above to provide a second extract.

The second extract is then concentrated by evaporation under nitrogen and separated by passage over normal phase, Supelco silica column (5 $\mu$; 4.6×250 mm) via a Waters liquid chromatograph system describe in Example I. A solvent system of hexane: methyl-t-butyl ether:isopropanol (60:40:10 v/v/v) is used to separate the lipid chemoattractant for other remaining contaminants. The lipid chemoattractant elutes at 18–20 minutes.

The concentrated lipid chemoattractant is now essentially pure and it may be pooled and used for a variety of purposes. Further purification of the lipid chemoattractant is still possible, however and is achieved by first preparing a third extract by the active fraction by under nitrogen, resuspending it in acetonitrile, and elution by passage of a Supelco LC-DP dipheny reversed phase HPLC column delivered via a Waters liquid chromatograph system as described in Example I. The same gradient of solvent (acetonitrile:water) is used as is described in Example I with the exception of the addition of 50 nM ammonium acetate.

The third extract is applied to a reversed phase C-18 guard column in 25% acetonitrile/75% $H_2O$. The column is then equilibrated in 100% water and the activity is then eluted in 100% acetonitrile moving a 1 ml/minute.

The lipid chemoattractant is further purified by loading onto Phenomenex cyanaopropyl column (3 $\mu$, 3 mm×150 mm) in hexane: methyl t-butyl ether (60:40 v/v), 1 ml/mm, with elution time of the activity being 3–5 minutes. These subsequent purification steps takes the essentially pure solution of lipid chemoattractant and results in a nearly homogeneous preparation of lipid chemoattractant as determined by NMR and MS testing.

EXAMPLE III

The sensitivity of the lipid chemoattractant to borohydride indicates the presence of a carbonyl group, which distinguishes it from long chain acetylenic enol ethers of glycerol. The presence of a carbonyl group on the backbone of the structure is supported by the observation that $C^{14}$-labeled dihydroxyacetone (DHA) is incorporated into the lipid chemoattractant. The 2(C) labeled $C^{14}$-DHA incorporation into the lipid chemoattractant has been demonstrated in two types of experiments. In the intact cell assay outlined in Example I, $C^{14}$-DHA is (100 μM) included with albumen-oleate in the medium of rat proximal renal tubules placed in short-term tissue culture where it is incorporated into the lipid chemoattractant. The labeled chemoattractant was then purified by the method detailed in Example II, and each fraction that demonstrated biological activity also demonstrated incorporation of $C^{14}$-DHA. Analogous results are observed in a cell free lipid chemoattractant-generating system consisting of 100 μM DHA, 50 μM oleyl alcohol, 10 MM ATF, 4 mM $MgCl_2$, 20 mM NADH, 33 mg/ml catalase, and 500 μg of microsomal protein from rat kidney cortex. Incubation of this mixture in Kreb's-Henseleit medium for one hour at 37° C. yields a lipid chemoattractant with DHA incorporation that is chromatographically and biochemically identical to that of the lipid chemoattractant isolated from intact kidney cells or proteinuric urine.

What is claimed is:

1. A method for detecting the presence of injured tissue in a human comprising collecting body fluid from a human, preparing an essentially pure lipid chemoattractant, and testing the resulting essentially pure chemoattractant product in a standard bioassay wherein the lipid chemoattractant has the following structure:

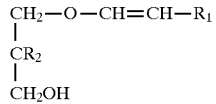

where $R_1$ is a $C_4$–$C_{22}$ alkyl group containing from 1 to 3 branched groups selected from the groups consisting of hydroxyl, oxygen, or carbonyl, and from 1 to 3 unconjugated double or triple bonds, wherein $R_2$ is =O, or —OH, and wherein $R_1$ and $R_2$ must include at least one carbonyl group or oxygen that is not part of a hydroxyl group.

2. The method of claim 1 wherein the an essentially pure lipid chemoattractant is prepared from the human body fluid by the steps comprising:

a. separating the body fluid using a silica-based separation technique to give a first separation product comprising the lipid chemoattractant and at least one fatty acid contaminant;

b. hydrolyzing the first separation product with an alkaline agent to give a hydrolyzed product comprising the lipid chemoattractant and cleaved fatty acid contaminants; and c. separating the lipid chemoattractant from the hydrolyzed product using silica-based separation techniques to give a second separation product comprising an essentially pure lipid chemoattractant.

3. The method of claim 1 wherein the injury is atherosclerosis and the body fluid is plasma.

4. The method of claim 1 wherein the injury is chronic kidney disease and the body fluid is selected from the group consisting of plasma and urine.

* * * * *